United States Patent [19]

Ashmead

[11] Patent Number: 5,292,729
[45] Date of Patent: Mar. 8, 1994

[54] Π-BOND AROMATIC VITAMIN CHELATES

[75] Inventor: Harvey H. Ashmead, Kaysville, Utah

[73] Assignee: Albion International, Inc., Clearfield, Utah

[21] Appl. No.: 930,747

[22] Filed: Aug. 14, 1992

[51] Int. Cl.$^5$ .................. A61K 33/24; C07D 401/14; C07D 417/14

[52] U.S. Cl. .................. 514/168; 514/188; 544/225; 546/8

[58] Field of Search ............ 546/8; 544/225; 514/168

[56] References Cited

U.S. PATENT DOCUMENTS

| | | | |
|---|---|---|---|
| 4,725,427 | 2/1988 | Ashmead et al. | 514/168 |
| 4,923,855 | 5/1990 | Jensen | 546/5 |
| 5,134,237 | 7/1992 | Rolf | 544/225 |
| 5,155,224 | 10/1992 | Rocklage et al. | 546/8 |

OTHER PUBLICATIONS

Mertz et al. Federation Proceedings, 23(11) pp. 2275-2280; 1974.

*Primary Examiner*—Mukund J. Shah
*Assistant Examiner*—P. K. Sripada
*Attorney, Agent, or Firm*—Thorpe, North & Western

[57] ABSTRACT

Vitamin and mineral absorption in warm-blooded animals is promoted by means of a class of vitamin chelates where at least one of the bonds between the metal ion and the vitamin ligand is formed between the ion and an electron rich π-cloud of an aromatic ring of the water soluble vitamin. The chelate, containing a total of from one to three ligands, may contain from one up to three vitamin ligands which form a π-bond with the mineral and, when present, one or two amino acid, dipeptide or tripeptide ligands. The mineral is selected from the group consisting of Fe, Cu, Zn, Mg, Mn and Ca. The water soluble vitamin ligand is preferably a residue of nicotinamide, nicotinic acid, pyridoxine, thiamine, riboflavin and folic acid. The amino acid may be any of the naturally occurring α-amino acids such as glycine. The π-bond vitamin chelates are absorbed more readily from both the gastric and intestinal areas of the GI tract than vitamins or minerals administered separately or as mixtures.

50 Claims, No Drawings

Π-BOND AROMATIC VITAMIN CHELATES

This invention relates to mineral chelates containing vitamin ligands wherein the ligand and mineral ion is bonded via at least one π-bonding mechanism. More particularly, this invention relates to mineral chelates containing as ligands, one or more water soluble vitamins with or without the presence of amino acids, wherein the vitamin ligand contains an aromatic ring and is at least partially bonded to the metal ion via π-cloud bonding.

BACKGROUND OF THE INVENTION AND STATE OF THE ART

The term "chelate" has often been misunderstood or applied in a general or catch-all fashion. A chelate is a definite structure resulting from precise requirement of synthesis. Proper conditions must be present for chelation to take place, including proper mole ratios of ligands to metal ions, pH and solubility of reactants. For chelation to occur, all components must be dissolved in solution and either be ionized or of appropriate electronic configuration in order for bonding to develop.

Chelation can be confirmed and differentiated from mixtures of components by infrared spectra through comparison of the stretching of bonds or shifting of absorption caused by bond formation.

As applied in the field of mineral nutrition, there are two allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, i.e. copper proteinate, zinc proteinate, etc. This definition does not contain any requirements to assure that chelation is actually present. On the basis of the chemical reactant possibilities, there are some real reservations as to the probability of chelation occurring to any great degree. For example, the inclusion of partially hydrolyzed proteins as suitable ligands and the term "and/or" in reference to such ligands implies that products made solely from partially hydrolyzed protein and soluble salts would have the same biochemical and physiological properties as products made from combining amino acids and soluble metal salts. Such an assertion is chemically incorrect. Partially hydrolyzed protein ligands may have molecular weights in the range of thousands of daltons and any bonding between such ligands and a metal ion may be nothing more than a complex or some form of ionic attraction, i.e. the metal drawn in close proximity to carboxyl moiety of such a ligand.

While some products marketed as metal proteinates during the 1960's and 1970's were true chelates, this was prior to the adoption of the AAFCO definition. An analysis of products currently marketed as metal proteinates reveals that most, if not all, are mixtures of metal salts and hydrolyzed protein or complexes between metal salts and hydrolyzed protein. Most are impure products which are difficult to analyze and are not consistent in protein make-up and/or mineral content.

The second product, referred to as an "amino acid chelate", when properly formed, is a stable, product having one or more five-membered ring formed by reaction between the carboxyl oxygen, and the α-amino group of an α-amino acid with the metal ion. Such a five-membered ring is defined by the metal atom, the carboxyl oxygen, the carbonyl carbon, the α-carbon and the α-amino nitrogen and is generally represented by the following formulae. However, the actual structure will depend upon the ligand to metal mole ratio. The ligand to metal mole ratio is at least 1:1 and is preferably 2:1 but, in certain instances may be 3:1 or even 4:1. Most typically, an amino acid chelate may be represented at a ligand to metal ratio of 2:1 according to the following formula:

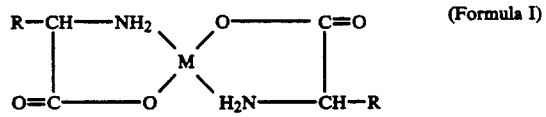
(Formula I)

In the above formula, when R is H, the amino acid is glycine which is the simplest of the α-amino acids. However, R could be representative of any other the other twenty or so naturally occurring amino acids derived from proteins. These all have the same configuration for the positioning of the carboxyl oxygen and the α-amino nitrogen. In other words, the chelate ring is defined by the same atoms in each instance. The American Association of Feed Control Officials (AAFCO) have also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, i.e. iron amino acid chelate, copper amino acid chelate, etc.

The reason a metal atom can accept bonds over and above the oxidation state of the metal is due to the nature of chelation. In Formula I it is noted that one bond is formed from the carboxyl oxygen. The other bond is formed by the α-amino nitrogen which contributes both of the electrons used in the bonding. These electrons fill available spaces in the d-orbitals. This type of bond is known as a dative bond or a coordinate covalent bond and is common in chelation. Thus, a metal ion with a normal valency of +2 can be bonded by four bonds when fully chelated. When chelated in the manner described the divalent metal ion is completely satisfied by the bonding electrons and the charge on the metal atom (as well as on the overall molecule) is zero. This neutrality contributes to the bioavailability of metal amino acid chelates.

Amino acid chelates can also be formed using peptide ligands instead of single amino acids. These will usually be in the form of dipeptides or tripeptides because larger ligands would have a molecular weight which would be too great for direct assimilation of the chelate formed. Generally, peptide ligands will be derived by the hydrolysis of protein. However, peptides prepared by conventional synthetic techniques or genetic engineering can also be used. When a ligand is a di- or tripeptide a radical of the formula $[C(O)CHRNH]_eH$ will replace one of the hydrogens attached to the nitrogen atom in Formula I. R, as defined in Formula I, can be H, or the residue of any other naturally occurring amino acid and e can be an integer of 1 or 2. When e is 1 the ligand will be a dipeptide and when e is 2 the ligand will be a tripeptide.

The structure, chemistry and bioavailability of amino acid chelates is well documented in the literature, e.g. Ashmead et al-., *Chelated Mineral Nutrition*, (1982), Chas. C. Thomas Publishers, Springfield, Ill.; Ashmead et al., *Intestinal Absorption of Metal Ions*, (1985), Chas. C. Thomas Publishers, Springfield, Ill.; Ashmead et al., *Foliar Feeding of Plants with Amino Acid Chelates*, (1986), Noyes Publications, Park Ridge, N.J. as well as in U.S. Pat. Nos. 4,020,158; 4,167,564; 4,216,143; 4,216,144; 4,599,152; 4,774,089; 4,830,716; 4,863,898 and others. Flavored effervescent mixtures of vitamins and amino acid chelates for administration to humans in the form of a beverage are disclosed in U.S. Pat. No. 4,725,427.

One advantage of amino acid chelates in the field of mineral nutrition is attributed to the fact that these chelates are readily absorbed in the gut and mucosal cells by means of active transport as though they were amino acids. In other words, the minerals are absorbed along with the amino acids as a single unit utilizing the amino acids as carrier molecules. Since this method of absorption does not involve the absorption sites for free metal ions, the problems of competition of ions for active sites and suppression of one nutritive mineral element by another are avoided.

The importance of vitamins and minerals in proper nutrition has long been recognized. However, it is generally thought that the absorption of vitamins and minerals is independent of each other. Even when marketing vitamin and mineral combinations, such as taught in U.S. Pat. No. 4,725,427, the vitamin and mineral ingredients are admixed and coadministered as separate entities.

There has been some discussion of some interaction between nicotinic acid, amino acids and chromium and niacinamide and cobalt in conjunction with certain amino acids and/or small peptides as they relate to components forming the glucose tolerance factor (GTF). Mertz et al., "Present Knowledge of the Role of Chromium", *Federation Proc.*, 23(11) pp. 2275-2280 (1974) reported that, in efforts to purify the GTF, there was detected chromium, nicotinic acid, glycine, glutamic acid and cysteine. A possible structure for a dinicotinato-amino acid Cr-complex was proposed consisting of approximately 2 moles each of nicotinic acid and glycine and one mole of cysteine per chromium atom. It was readily acknowledged that the exact structure was not known. Toepfer et al., "Preparation of Chromium-Containing Material of Glucose Tolerance Factor Activity from Brewer's Yeast Extracts and by Synthesis", *J. Agric. Food Chem.*, 25(1) pp. 162-166 (1977) report the synthesis of a chromium complex containing two moles nicotinic acid, 2 moles glycine, 1 mole glutamic acid and 1 mole of cysteine per chromium atom. Further reported is the formation of complexes of chromium with nicotinic acid alone in a presumably dinicotinato, tetaaquo configuration. This complex was stated to be unstable and rapidly lost biological activity. The formation of other complexes of chromium and nicotinic acid with other amino acids was alluded to but not specifically demonstrated. While Toepfer et al. reported GTF type biological activity it was stressed that the structure of the complexes formed was only speculative. Silio, "Process for Obtaining a New Glucose Tolerance Factor", U.S. Pat. No. 4,242,257 (1980) suggests the formation of a complex between cobalt and nicotinamide which is then reacted with the tripeptide, glutathione, to form a product having GTF activity. No structure is proposed and the reaction must be carried out stepwise with the complex between the chromium salt and nicotinamide first being formed, acidified and then reacted with glutathione.

An excellent summary of the state of the art relative to the structure and synthesis of complexes exhibiting GTF activity is found in Jensen, Synthetic GTF Chromium Material and Process Therefor, U.S. Pat. No. 4,923,855 (1990). Jensen lists several proposed structures including chromium and nicotinic acid showing dative or coordinate covalent bonding between the nitrogen atom of the pyridine ring and also involving the carboxyl oxygen of the —COO⁻ of the nicotinic acid. Jensen quite clearly states that the structure formed from the reaction of nicotinic acid and chromium is not known with any degree of certainty. A proposed reaction sequence is given on col . 5 and a trinicotinate structure is proposed at the top of col. 6. However, it is stated at lines 25-38 of col. 6 that it is likely that the reaction illustrated does not go to completion. It is speculated that some dinicotinate and perhaps even some mononicotinate or even pentanicotinate may be formed.

Weismann, "Chelating Drugs and Zinc", *Dan. Med. Bul.*, 33 208-211 (1986) states that, in nature, there are various vitamin-metal complexes formed such as Zn-thiamine, Zn-pyridoxamine and Zn-biotin. Several "drugs" are also mentioned and structures are proposed for Zn-drug complexes, none of which involve vitamins. However, each structure proposed shows the conventionally described chelate bond, i.e. between the zinc ion and an amine or OH group. No $\pi$-cloud or resonance bonding is taught or even suggested.

While the above mentioned complexes and chelates are of interest both from the standpoint of their biological activity and structure, they are limited in scope to certain types of activity and, for the most part, involve only the metal ions Co and Cr which are present in only very minute amounts in complexes exhibiting GTF type activity or in alleged naturally occurring Zn vitamin complexes. It would be desirous to formulate a class of chelates which would simultaneously provide the benefits of vitamins and a broad class of the minerals most commonly required in biosystems, e.g. Fe, Cu, Mn, Zn, Ca and Mg, combined in a single molecule having superior bioavailability for both mineral and vitamin.

OBJECTS AND BRIEF SUMMARY OF THE INVENTION

It is an object of the present invention to provide a class of mineral vitamin chelates which provides improved absorption of both the vitamin and the mineral.

It is also an object of the invention to provide a class of mineral vitamin chelates having greater stability and which may, in certain instances, provide mineral absorption by means of transport through the stomach lining in addition to the intestinal tract.

These and other objects may be accomplished by a class of vitamin chelates wherein at least one of the bonds between the metal ion and the vitamin ligand is formed between the ion and an electron rich $\pi$-cloud of an aromatic ring of the vitamin. Obviously, in order for the vitamin to function as a ligand in the present invention it is essential that the ligand structure is conducive to the formation of a five or six member ring formed using, in consecutive order, the $\pi$-cloud of the aromatic ring, the metal ion, a carbon containing moiety of one or two carbon atoms, an O, S, or N atom and a carbon atom of the aromatic ring. The chelate, containing from one to three total ligands, may contain one to three vitamin ligands and may also contain up to two amino acid ligands. The term "amino acid ligand" is also inclusive of di- and tripeptide ligands. Preferably the chelate will contain two or three ligands one of which must be that of a water soluble vitamin having an electron rich aromatic ring through which a $\pi$-cloud bond may be formed with the mineral. The vitamin chelate may be represented by the formula:

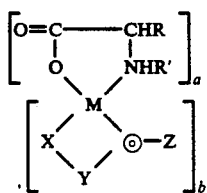

(Formula II)

wherein a is an integer of 0, 1 or 2, b is an integer of 1, 2 or 3, with the proviso that the sum of a and b does not exceed 3, X is a member selected from the group consisting of OH, SH and $NH_2$, Y is a member selected from the group consisting of $CH_2$, $CH_2CH_2$, and C(O), ⊙ is an aromatic ring of a water soluble vitamin and Z is the residue of the water soluble vitamin not defined by X, Y and ⊙ with the proviso that ⊙, Y and X are configured to form a five or six membered ring structure when bonded to M; R is the residue of any naturally occurring α-amino acid, R' is a member selected from the group consisting of H and $[C(O)CHRNH]_eH$, where e is an integer of 1 or 2 and R is as defined above and M is a metal ion selected from the group consisting of Fe, Cu, Mg, Zn, Ca and Mn. Preferably, Z-⊙, Y and X will be the residue of a water soluble vitamin selected from the group consisting of nicotinamide, nicotinic acid, pyridoxine, thiamine, riboflavin and folic acid. M is preferably a metal ion selected from one of two groups, i.e. the group consisting of Cu, Mn and Fe and the group consisting of Zn, Ca and Mg. The Cu, Mn and Fe group has some greater flexibility regarding the number of ligands which will attach thereto, i.e. from one to three, whereas the Zn, Ca and Mg group of minerals will usually form a chelate containing one or two ligands. R' will preferably be H but the utilization of di- or tripeptide ligands, i.e. e being 1 or 2, is also considered to be an important facet of the invention. When a is 2 the amino acid ligands bonded to the metal ion M may be the same or different. Also, mixtures of amino acids ligands used in forming the chelate are also contemplated within the scope of the invention.

DETAILED DESCRIPTION OF THE INVENTION AND A PREFERRED EMBODIMENT

The vitamin chelates of the present invention differ from previously known chelates in that, instead of an electronegative atom forming a coordinate-covalent bond, that bond is replaced by a bond formed between the metal ion and the $\pi$-cloud of the aromatic ring of the vitamin. Because $\pi$-clouds are rich in electrons, they behave as nucleophiles. When $\pi$-cloud types of chelates are formed between the aromatic ring of a water soluble vitamin and a metal ion, greater stability and enhanced absorption and utilization (i.e. increased bioavailability) are observed for both the metal and the vitamin.

Iron (III) or manganese (II) may be used as illustrative of the type of $\pi$-cloud bonding which occurs in the formation of the chelates disclosed herein. If iron (III) or manganese (II) exists as the $Fe^{3+}$ and $Mn^{2+}$ ions respectively, according to valence bond theory, the valence or unfilled orbitals seeking electrons are in the 3d orbitals as follows ( ↑ )( ↑ )( ↑ )(  )(  ). When electron rich ligands attach to $Fe^{3+}$ or $Mn^{2+}$ ions they can provide electron pairs which fill the remaining two 3d orbitals, one 4s and three 4p orbitals. This produces an octahedral geometry and a $d^2sp^3$ hybridization of the $Fe^{3+}$ or $Mn^{2+}$ ions.

In order to produce a chelate having the desired properties, from one to three bidentate ligands, at least one being a vitamin capable of $\pi$-cloud bonding, must provide two electron pairs to overlap with the $d^2sp^3$ hybridized orbitals. The lone pair of electrons on a $\ddot{N}$, $\ddot{O}$ or $\ddot{S}$ atom may serve as one electron pair and the $\pi$-cloud on the vitamin aromatic ring may serve as the other electron pair when the ligand is a vitamin. When the ligand is an amino acid, the amide nitrogen and the carboxyl oxygen provide the electron pairs in the usual manner. Using nicotinamide, glycine and $Fe^{3+}$ as representative examples, the electron pairs of the nicotinamide nitrogen and the $\pi$-cloud electrons of the pyridine ring overlap with the $d^2sp^3$ hybridized orbitals of the $Fe^{3+}$ ion forming a ring which contains two $sp^2$ hybridized carbons, and $sp^3$ hybridized nitrogen, a $d^2sp^3$ hybridized $Fe^{3+}$ ion and a $\pi$-cloud from the pyridine ring. Glycine also acts as a bidentate ligand in its usual manner to form a chelate having the formula:

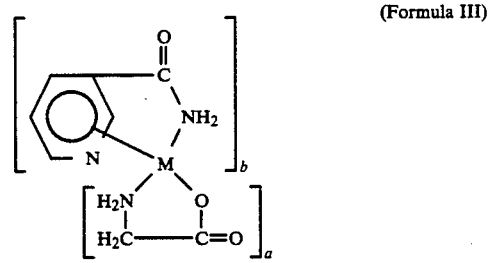

(Formula III)

The following examples are illustrative of numerous $\pi$-bond vitamin mineral chelates falling within the scope of the present invention and means of their preparation. The data presented shows the best mode presently known of practicing the invention using nicotinic acid as the ligand through which the $\pi$-bond is formed and glycine as the amino acid of choice.

In the Examples 1-15 the $\pi$-bond chelates will generally correspond to Formula IV as follows:

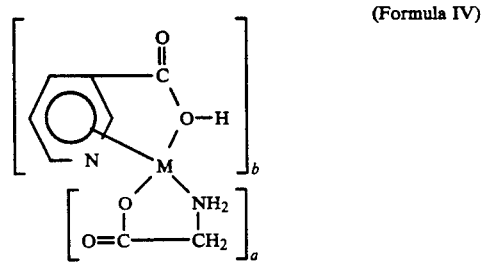

(Formula IV)

wherein b is an integer of 1, 2 or 3 and a is an integer of 0, 1 or 2 with the proviso that when a is 0 b will preferably be at least 2 and wherein M is any metal selected from the group consisting of Fe, Cu, Mg, Zn, Mn and Ca. M is preferably a metal ion selected from the group consisting either of Cu, Mn and Fe or Zn, Ca and Mg.

EXAMPLE 1

To a solution of 0.34 g (2.5 mmole) of $ZnCl_2$ in 0.34 g of water was slowly added 0.48 g (5 mmole) of sodium glycinate in 0.96 g of water. The solution remained clear for a few seconds and then became cloudy. A small amount of a white precipitate formed. This precipitate is a conventional amino acid chelate as shown in Formula I where R is H and M is Zn [or in Formula IV where a is 2 and b is 0 and M is Zn] and was prepared for comparison purposes.

EXAMPLE 2

To a solution of 0.34 g (2.5 mmole) of $ZnCl_2$ in 0.34 g of water was slowly added 0.24 g (2.5 mmole) of sodium glycinate and 0.36 g (2.5 mmole) of sodium nicotinate in 1.2 g of water. The solution turned white within a few seconds and a heavy white precipitate formed corresponding to Formula IV where a is 1, b is 1 and M is Zn.

EXAMPLE 3

To a solution of 0.34 g (2.5 mmole) of $ZnCl_2$ in 0.34 g of water was slowly added 0.72 g (5 mmole) of sodium nicotinate in 1.44 g of water. The solution turned white within a few seconds and a heavy, very thick, white precipitate formed corresponding to Formula IV where a is 0, b is 2 and M is Zn.

When studied by IR spectra, it was found that the shift of the single absorption band in nicotinic acid at 1708 $cm^{-1}$ resolved to two absorption sites in the zinc dinicotinate $\pi$-cloud chelate. The symmetric stretch appears at about 1640 $cm^{-1}$ while the asymmetric stretch is at 1730 $cm^{-1}$. The absorption found at 1035 $cm^{-1}$ in nicotinic acid is not observed in the chelate.

EXAMPLE 4

A solution of 0.43 g (2.5 mmole) of $CuCl_2 \cdot 2H_2O$ in 0.43 g of water was prepared which was green in color. To this was slowly added 0.72 g (7.5 mmole) of sodium glycinate in 1.44 g of water. A deep blue precipitate formed immediately. This precipitate is a conventional amino acid chelate similar to that shown in Formula I where R is H and M is Cu but having a glycine to Cu mole ratio of 3:1 [or in Formula IV where a is 3, b is 0 and M is Cu] and was prepared for comparison purposes.

EXAMPLE 5

A solution of 0.43 g (2.5 mmole) of $CuCl_2 \cdot 2H_2O$ in 0.43 g of water was prepared which was green in color. To this was slowly added 0.48 g (5 mmole) of sodium glycinate and 0.36 g (2.5 mmole) of sodium nicotinate in 2.04 g of water. A deep blue precipitate, slightly lighter in color than that formed in Example 4 formed immediately. This precipitate corresponds to Formula IV where a is 2, b is 1 and M is Cu.

EXAMPLE 6

A solution of 0.43 g (2.5 mmole) of $CUCl_2 \cdot 2H_2O$ in 0.43 g of water was prepared as in Example 5. To this was slowly added 0.24 g (2.5 mmole) of sodium glycinate and 0.72 g (5 mmole) of sodium nicotinate in 1.92 g of water. A blue precipitate, lighter in color than that formed in Example 5 formed immediately. This precipitate corresponds to Formula IV where a is 1, b is 2 and M is Cu.

EXAMPLE 7

A solution of 0.43 g (2.5 mmole) of $CuCl_2 \cdot 2H_2O$ in 0.43 g of water was prepared as in Example 5. To this was slowly added 0.96 g (7.5 mmole) of sodium nicotinate in 1.92 g of water. A very light blue precipitate, lighter in color than that formed in Example 6, formed immediately. This precipitate corresponds to Formula IV where a is 0, b is 3 and M is Cu.

EXAMPLE 8

A solution of 0.68 g (2.5 mmole) of $FeCl_3 \cdot 6H_2O$ in 0.68 g of water was prepared which was yellow in color. To this was slowly added 0.72 g (7.5 mmole) of sodium glycinate in 1.44 g of water. A dark brown solution resulted but no precipitate formed. This solution contained a soluble conventional amino acid chelate similar to that shown in Formula I where R is H and M is Fe but having a glycine to Fe mole ratio of 3:1 [or in Formula IV where a is 3, b is 0 and M is Fe] and was prepared for comparison purposes.

EXAMPLE 9

A solution of 0.68 g (2.5 mmole) of $FeCl_3 \cdot 6H_2O$ in 0.68 g of water was prepared to which was slowly added 0.48 g (5 mmole) of sodium glycinate and 0.36 g (2.5 mmole) of sodium nicotinate in 2.04 g of water. A brown precipitate formed. This precipitate corresponds to Formula IV where a is 2, b is 1 and M is Fe.

EXAMPLE 10

A solution of 0.68 g (2.5 mmole) of $FeCl_3 \cdot 6H_2O$ in 0.68 g of water was prepared to which was slowly added 0.24 g (2.5 mmole) of sodium glycinate and 0.72 g (5 mmole) of sodium nicotinate in 1.92 g of water. A brown precipitate formed. This precipitate corresponds to Formula IV where a is 1, b is 2 and M is Fe.

EXAMPLE 11

A solution of 0.68 g (2.5 mmole) of $FeCl_3 \cdot 6H_2O$ in 0.68 g of water was prepared to which was slowly added 0.96 g (7.5 mmole) of sodium nicotinate in 1.92 g of water. A brown precipitate formed. This precipitate corresponds to Formula IV where a is 3, b is 0 and M is Fe.

EXAMPLE 12

A solution of 0.49 g (2.5 mmole) of $MnCl_2 \cdot 4H_2O$ in 0.49 g of water was prepared to which was slowly added 0.72 g (7.5 mmole) of sodium glycinate in 1.44 g of water. A cream colored precipitate formed. The solution exposed to air turned dark brown on its surface. The precipitate consisted of a conventional amino acid chelate similar to that shown in Formula I where R is H and M is Mn but having a glycine to Mn mole ratio of 3:1 [or in Formula IV where a is 3, b is 0 and M is Mn] and was prepared for comparison purposes.

EXAMPLE 13

A solution of 0.49 g (2.5 mmole) of $MnCl_2 \cdot 4H_2O$ in 0.49 g of water was prepared to which was slowly added 0.48 g (5 mmole) of sodium glycinate and 0.36 g (2.5 mmole) of sodium nicotinate in 2.04 g of water. An off-white precipitate formed. The solution exposed to air turned dark brown on its surface. The precipitate corresponds to Formula IV where a is 2, b is 1 and M is Mn.

EXAMPLE 14

A solution of 0.49 g (2.5 mmole) of $MnCl_2 \cdot 4H_2O$ in 0.49 g of water was prepared to which was slowly added 0.24 g (2.5 mmole) of sodium glycinate and 0.72 (5 mmole) of sodium nicotinate in 1.92 g of water. An off-white precipitate formed. The solution exposed to air turned dark brown on its surface. The precipitate corresponds to Formula IV where a is 1, b is 2 and M is Mn.

EXAMPLE 15

A solution of 0.49 g (2.5 mmole) of $MnCl_2 \cdot 4H_2O$ in 0.49 g of water was prepared to which was slowly added 0.96 g (7.5 mmole) of sodium nicotinate in 1.92 g of water. A pure white precipitate formed. The solution exposed to air did not turn brown on its surface as in Examples 15–17. The precipitate corresponds to Formula IV where a is 0, b is 3 and M is Mn.

The invention is not limited solely to the embodiments specifically exemplified above. Other water soluble vitamins having aromatic ring structures capable of forming $\pi$-bonds may also be used as shown by the following examples.

EXAMPLE 16

Pyridoxine may act as a chelating ligand and forms a five membered ring in which one OH group provides a lone pair of electrons to form a coordinate covalent bond and a $\pi$-cloud complex is formed with the pyridine ring.

A pyridoxine:glycine:zinc chelate having a molecular ratio of 1:1:1 was prepared. To a solution of 0.34 g (2.5 mmole) of $ZnCl_2$ in 0.34 g of water was slowly added 0.24 g (2.5 mmole) of sodium glycinate and 0.42 g (2.5 mmole) of pyridoxine in 1.5 g of water. The precipitate formed was dissolved in ethanol and refrigerated. Pure chelate crystals formed having a melting point of about 70° C., a pH of about 3.9 and a solubility in water of about 10.4 mg/ml at room temperature.

This chelate corresponds to Formula II wherein M is Zn, a is 1, R is H, b is 1. Z-Ⓞ, Y and X represent the residue of pyridoxine with X being OH, Y being $CH_2$, Ⓞ is a pyridine ring and Z represents the 5-methyl, 4-hydroxy and 3-hydroxymethyl substituents on the pyridine ring.

This chelate has the $\pi$-cloud structure:

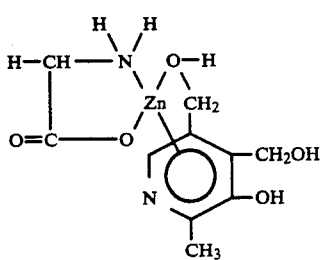

The presence of chelation was confirmed by IR spectra. The C—O absorption is shifted from its normal position at 1080 $cm^{-1}$ in pure pyridoxine to 1110 $cm^{-1}$. This shift is due to the oxygen attachment to the metal ion.

EXAMPLE 17

A pyridoxine zinc chelate having a ligand to zinc mole ratio of 2:1 is prepared corresponding to Formula II wherein a is 0 and b is 2 and with Z-Ⓞ, Y and X being the residue of pyridoxine as defined in Example 16. To a solution of 0.34 g (2.5 mmole) of $ZnCl_2$ in 0.34 g of water was slowly added 0.84 g (5 mmole) of pyridoxine in 1.5 g of water. A precipitate formed corresponding to the formula:

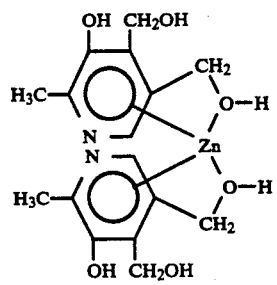

EXAMPLE 18

Nicotinamide may act as a chelating ligand and forms a five membered ring in which the NH group of the amide provides a lone pair of electrons to form a coordinate covalent bond and a $\pi$-cloud complex is formed with the pyridine ring. A chelate of nicotinamide:glycine:zinc having a molecular ratio of 1:1:1 was prepared corresponding to Formula II wherein a is 1 and b is 1 and with Z-Ⓞ, Y and X being the residue of nicotinamide wherein X is $NH_2$, Y is C(O) and Ⓞ-Z is a pyridine ring. To a solution of 0.34 g (2.5 mmole) of $ZnCl_2$ in 0.34 g of water was slowly added 0.24 g (2.5 mmole) of sodium glycinate and 0.31 g (2.5 mmole) of nicotinamide in 1.5 g of water. The precipitate formed was dissolved in ethanol and refrigerated. This chelate has the $\pi$-cloud structure:

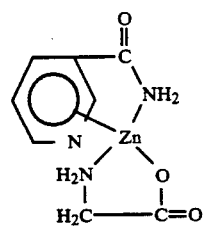

EXAMPLE 19

A nicotinamide zinc chelate having a ligand to zinc mole ratio of 2:1 was prepared corresponding to Formula II wherein a is 0 and b is 2 and with Z-Ⓞ, Y and X being the residue of nicotinamide as defined in Example 18. To a solution of 0.34 g (2.5 mmole) of $ZnCl_2$ in 0.34 g of water was slowly added 0.61 g (5 mmole) of nicotinamide in 1.5 g of water. No precipitate formed and 10 drops of ethanol was slowly dropped, one drop at a time, into a test tube holding this solution until a milky precipitate haze formed. The solution was warmed slightly to dissolve the precipitated crystals and the inside of the test tube was scratched with a glass stirring rod. The test tube was let stand overnight resulting in the formation of a significant amount of crystals. The crystals were washed with ice water to remove contaminants yielding a π-cloud chelate corresponding to the formula:

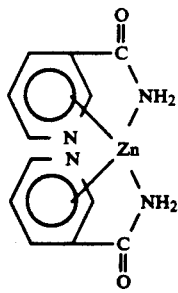

When analyzed by IR spectra it was found that the N—H absorption band, normally found at about 3380 cm$^{-1}$ in pure nicotinamide, was shifted to about 3410 cm$^{-1}$ in the chelate. The shifts in the N—H bending at 680 cm$^{-1}$ and 745 cm$^{-1}$ in the chelate is different from the absorptions observed at 710 and 780 cm$^{-1}$ respectively in pure nicotinamide. The shift is due primarily to the attachment of the amide nitrogen to the zinc.

EXAMPLE 20

Thiamine may act as a chelating ligand and forms a five membered ring in which the OH group of the hydroxyethyl chain on the thiazole ring provides a lone pair of electrons to form a coordinate covalent bond and a π-cloud complex is formed with the thiazole ring. A thiamine:glycine:zinc chelate having a molecular ratio of 1:1:1 was prepared corresponding to Formula II wherein M is Zn, a is 1, R is H and b is 1. Z-⊙, Y and X represent the residue of thiamine with X being OH, Y being CH$_2$CH$_2$, ⊙ being a thiazole ring and Z representing the 3-[(4-amino-2-methyl-5-pyrimidinyl)methyl and 4-methyl substituents on the thiazole ring.

To a mixture of 0.34 g (2.5 mmole) of ZnCl$_2$ in 0.34 g of water was slowly added 0.24 g (2.5 mmole) of sodium glycinate and 0.84 g (2.5 mmole) of thiamine hydrochloride in 1.5 g of water. About 0.06 ml of H$_3$PO$_4$ was added and the mixture was heated to 70° C. where it became a clear solution. The solution was washed with ethanol and no precipitate formed. The solution was placed in a refrigerator overnight and was then placed on a workbench at room temperature. Within an hour after being removed from the refrigerator, crystals precipitated from the solution. The crystals has a melting point of about 145°-155° C., a solubility of about 10 mg/ml. The pH of a saturated solution was about 2.4. When ZnCl$_2$ was replaced with 2.5 mm (0.40 g) of ZnSO$_4$ and the same procedure was followed, the recrystallized product melted between about 200°-205° C., had about the same solubility but had a pH of about 2.9. There was obviously some difference caused in either the purity or the structure resulting from the use of a chloride salt as compared to a sulfate. These differences are currently under investigation. However, IR spectra showed that chelation had occurred. The chelate formed is believed to have the π-cloud structure:

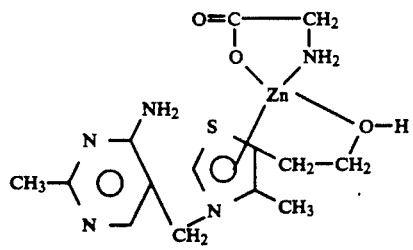

The IR spectra of thiamine and glycine chelated with zinc shows the following changes when compared to the raw components. The O—H stretching absorption in the metal chelate appears at 3220 cm$^{-1}$ and there is no exactly corresponding peak in either glycine or thiamine. The new absorption at 3080 cm$^{-1}$ is evidence of the metal bonding to the π-cloud of the thiazole ring. The shift in the NH$_2$ peaks at 3505 and 3445 cm$^{-1}$ is believed to be due to the coordinate-covalent bond formed between the amino nitrogen of the glycine and the metal ion. The absorption at 1075 cm$^{-1}$ is thought to be due to the C—O bond stretching in the C—O—ZN portion of the chelate as this does not appear in this position in pure thiamine. The 1035 cm$^{-1}$ absorption is considered due to the C—N bond in glycine in the chelate and is slightly shifted from 1030 cm$^{-1}$ in pure glycine.

EXAMPLE 21

A thiamine zinc chelate having a ligand to zinc mole ratio of 24 is prepared corresponding to Formula II wherein a is 0 and b is 2 and with Z-⊙, Y and X being the residue of thiamine as defined in Example 20. The procedure essentially following that used in Example 20 except that 5.0 mmole of thiamine is used and glycine is deleted. ZNSO$_4$ is used as the zinc salt. The resulting π-bond chelate has the structure:

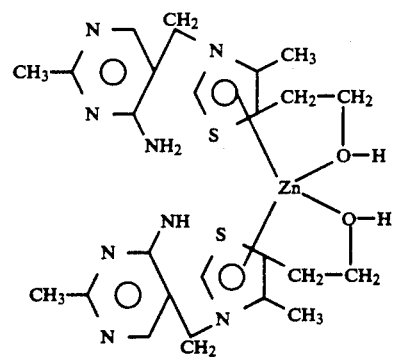

EXAMPLE 22

A zinc:glycine:nicotinamide chelate was prepared by reacting equimolar amounts glycine and nicotinamide with a ZnCl$_2$, $^{65}$ZnCl$_2$ mixture. On a w/v basis, 6.75 grams of glycine and 11.00 grams of nicotinamide and 6.25 grams of the ZnCl$_2$ mixture were dissolved in 86 mls of water containing 3 mls of reagent grade H$_2$SO$_4$. The chelate thus prepared was diluted such that a 5 μl dose contained about 0.03 mg Zn and 15 μcuries of $^{65}$Zn activity. This dose, when administered to a standard laboratory rat weighing 150±25 gms, closely approximates the RDA of 15 mg Zn for a human being weighing about 70 kg.

Ten Sprague Dawley rats, weighing 190±10 grams each were divided into two groups of five rats. Five rats were designated the test group and the other five rats the control group.

To the test group was orally administered, by gastric lavage, 5 μl of the test solution of the zinc:glycine:-nicotinamide chelate referenced above. The control group received the same amount of zinc (0.03 mg) and $^{65}$Zn activity (15 μcuries) in the form of ZnCl$_2$. No surgery was performed as all animals were given light doses of nembutal (40 mg/kg) to improve ease of handling and minimize injury during lavage and bloodletting.

Beginning 30 minutes after dosing and continuing at 30 minute intervals up to a period of 3 hours following dosing, 0.1 ml of blood was withdrawn from rats in both the test and control groups. The blood was then analyzed for $^{65}$Zn by scintillation count. The averaged results for each group are recorded in terms of corrected counts per minute (CCPM) with the ± standard deviation are given in Table 1 as follows:

TABLE 1

| Time (hrs) | Test | Control |
|---|---|---|
| 0.5 | 225 ± 5 | 210 ± 11 |
| 1.0 | 219 ± 17 | 226 ± 14 |
| 1.5 | 224 ± 12 | 212 ± 26 |
| 2.0 | 230 ± 14 | 227 ± 18 |
| 2.5 | 229 ± 16 | 206 ± 8 |
| 3.0 | 227 ± 11 | 207 ± 8 |

When subjected to statistical analysis using the three-factor hierarchal design program taken from Winer, *Statistical Principles of Experimental Design*, 2nd Ed. (1971), the difference in zinc levels between the test and control groups at 0.5, 2.5 and 3.0 hours was found to be statistically significant. The importance of this is that the higher zinc levels at 0.5 hours resulting from the chelated zinc indicates significant enhanced zinc absorption from the gastric area or stomach of the rats. The higher zinc levels at 2.5 and 3.0 hours further indicates prolonged or sustained zinc absorption from the chelated zinc as compared to the zinc salt.

It is therefore evident that, as the zinc migrated through the gastrointestinal tract, the zinc:glycine:-nicotinamide chelate demonstrated quicker and higher levels of gastric absorption as well as sustained levels of intestinal release when compared to the zinc chloride salt.

EXAMPLE 23

The rats used in Example 22 were sacrificed after completion of the testing and the urine, liver, muscle, kidney, brain and spleens from the animals in each grouping were collected for comparative $^{65}$zinc isotope levels. The results, again in CCPM, are given in Table 2 as follows:

TABLE 2

| Sample | Test | Control |
|---|---|---|
| Urine | 0 | 38 |
| Liver | 70 | 50 |
| Muscle | 0 | 0 |
| Kidney | 45 | 24 |
| Brain | 0 | 0 |
| Spleen | 37 | 16 |

Table 2 demonstrates that, with the exception of urine, there were significantly higher $^{65}$Zn levels in the tissues of the animals receiving the chelated zinc. No zinc isotope was found in the brain or muscle samples. The high zinc level in the urine of the control group indicates that the inorganic form of zinc is excreted more readily than the chelated form. Further, the higher zinc levels in the liver, kidney and spleen demonstrate greater zinc uptake into tissues from the chelated form of zinc as compared to the zinc salt.

The above examples, in which glycine is used as the amino acid ligand, could be reproduced employing any other of the naturally occurring α-amino acids, e.g. arginine, alanine, asparagine, aspartic acid, cysteine, cystine, glutamine, glutamic acid, histidine, hydroxyproline, isoleucine, leucine, lysine, methionine, ornithine, phenylalanine, proline, serine, threonine, tryptophan, tyrosine and valine and dipeptide and tripeptide of these, including glycine. The limiting factor is that the molecular weight of the entire π-bond vitamin, amino acid chelate molecule should not exceed 1500 daltons and will preferably not exceed 1000 and most preferably not be above 800 daltons. In addition, the stability constant should be sufficiently high that the chelate will pass intact through a acidic media of the stomach and, the portion not assimilated there, pass into the intestinal tract as an intact molecule. Sufficient data has not yet been developed to state with precision what the stability constant of these chelates will be but, based on amino acid chelates only, it will preferably is be between about $10^6$ and $10^{16}$. When deciding which amino acid, dipeptide or tripeptide to use as a ligand, attention is directed to the disclosure of Ashmead et al., U.S. Pat. No. 4,863,898, "Amino Acid Chelated Compositions for Delivery to Specific Biological Tissue Sites".

The examples which follow illustrate an embodiment of the invention wherein the amino acid ligand source used to form a chelate is a hydrolyzed vegetable protein (HVP) containing 85% amino acids and having an average amino acid molecular weight of about 130. The HVP utilized had the amino acid composition given in Table 3:

TABLE 3

| Amino Acid | Mass Percent | Mole Percent |
|---|---|---|
| Alanine | 4.3 | 6.3 |
| Arginine | 7.6 | 5.7 |
| Aspartic Acid | 11.6 | 11.3 |
| Cysteine | 1.3 | 1.4 |
| Glutamic Acid | 19.1 | 13.9 |
| Glycine | 4.2 | 7.2 |
| Histidine | 2.6 | 2.2 |
| Isoleucine | 4.9 | 4.9 |
| Leucine | 8.2 | 8.1 |
| Lysine | 6.3 | 5.6 |
| Methionine | 1.3 | 1.1 |
| Phenylalanine | 5.2 | 4.1 |
| Proline | 5.1 | 5.7 |
| Serine | 5.2 | 6.4 |
| Threonine | 3.8 | 4.1 |
| Tryptophan | 1.3 | 0.8 |
| Tyrosine | 3.8 | 2.7 |
| Valine | 5.0 | 5.5 |

Chelates formed using the above listed HVP as one ligand and nicotinic acid as the π-bond vitamin ligand would correspond to Formula V as follows:

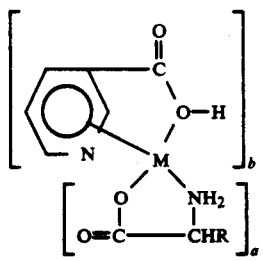
(Formula V)

wherein a, b, M and R are as defined above in Formula II, i.e. a is an integer of 0, 1 or 2, b is an integer of 1, 2 or 3 wherein the sum of a+b does not exceed 3, R is the residue of a naturally occurring amino acid and M is either Fe, Cu, Mg, Zn, Ca or Mn.

EXAMPLE 24

A 15.3 gram sample of the above HVP containing 13.0 grams of amino acids (0.1 mole) was dissolved in 80.7 g of water containing 4.0 g of sodium hydroxide forming a cloudy, yellow solution. This solution was added slowly to 13.6 g (0.1 mole) of $ZnCl_2$ and 4.0 g (0.1 mole) of sodium hydroxide in 82.3 g of water with stirring. A light yellow precipitate formed immediately. To this was added 12.3 g (0.1 mole) of nicotinic acid in 83.7 g of water and 4.0 (0.1 mole) of NaOH. The resulting mixture had a pH of 7 and was very light yellow in color. When the material was centrifuged, the light yellow precipitate occupied about half of the volume. Unlike the original HVP solution, the liquid above the precipitate was very clear.

The resulting chelate corresponds to Formula V wherein a and b are each 1, M is Zn and R is the residue of the amino acids listed in Table 3 wherein each amino acid is present in its respective mole percent.

EXAMPLE 25

A HVP solution made up of a 15.3 g sample of HVP was utilized as in Example 24. This solution was slowly added with stirring to a solution containing 13.4 g (0.1 mole) of $CuCl_2$ in 86.6 g of water. The solution immediately formed a blue precipitate. To this was added 24.6 g (0.2 moles) of nicotinic acid in 67.4 g of water and 8.0 g (0.2 moles) of NaOH. A lighter blue precipitate resulted corresponding to Formula V wherein a is 1, b is 2, M is Cu and R is the residue of the amino acids listed in Table 3 wherein each amino acid is present in its respective mole percent.

EXAMPLE 26

A HVP solution was made up of a 30.6 g sample of HVP dissolved in 61.3 g of water containing 8.0 g (0.2 moles) of NaOH. This solution was slowly added with stirring to a solution containing 13.4 g (0.1 mole) of $CuCl_2$ in 86.6 g of water. This solution also immediately formed a blue precipitate. To this was added 12.3 g (0.1 moles) of nicotinic acid in 83.7 g of water and 4.0 g (0.1 moles) of NaOH. As in Example 25 lighter blue precipitate resulted. This precipitate corresponds to Formula V wherein a is 2, b is 1, M is Cu and R is the residue of the amino acids listed in Table 3 wherein each amino acid is present in its respective mole percent.

EXAMPLE 27

A HVP solution made up of a 15.3 g sample of HVP was dissolved in 80.7 g of water containing 4.0 g (0.1 mole) of NaOH. This solution was slowly added with stirring to a solution containing 16.2 g (0.1 mole) of $FeCl_3$ in 83.8 g of water. The solution immediately formed a brown precipitate. To this was added 24.6 g (0.2 moles) of nicotinic acid in 67.4 g of water and 8.0 g (0.2 moles) of NaOH. A brown precipitate resulted corresponding to Formula V wherein a is 1, b is 2, M is Fe and R is the residue of the amino acids listed in Table 3 wherein each amino acid is present in its respective mole percent.

EXAMPLE 28

A HVP solution was made up of a 30.6 g sample of HVP dissolved in 61.3 g of water containing 8.0 g (0.2 moles) of NaOH. This solution was slowly added with stirring to a solution containing 16.2 g (0.1 mole) of $FeCl_3$ in 83.8 g of water. This solution also immediately formed a brown precipitate. To this was added 12.3 g (0.1 moles) of nicotinic acid in 83.7 g of water and 4.0 g (0.1 moles) of NaOH. As in Example 27, a brown precipitate resulted. This precipitate corresponds to Formula V wherein a is 2, b is 1, M is Fe and R is the residue of the amino acids listed in Table 3 wherein each amino acid is present in its respective mole percent.

EXAMPLE 29

A HVP solution made up of a 15.3 g sample of HVP was dissolved in 80.7 g of water containing 4.0 g (0.1 mole) of NaOH. This solution was slowly added with stirring to a solution containing 12.6 g (0.1 mole) of $MnCl_2$ in 87.4 g of water. The solution immediately formed a light yellow precipitate. To this was added 24.6 g (0.2 moles) of nicotinic acid in 67.4 g of water and 8.0 g (0.2 moles) of NaOH. A very light yellow precipitate resulted corresponding to Formula V wherein a is 1, b is 2, M is Mn and R is the residue of the amino acids listed in Table 3 wherein each amino acid is present in its respective mole percent.

EXAMPLE 30

A HVP solution was made up of a 30.6 g sample of HVP dissolved in 61.3 g of water containing 8.0 g (0.2 moles) of NaOH. This solution was slowly added with stirring to a solution containing 12.6 g (0.1 mole) of $MnCl_2$ in 83.8 g of water. This solution also immediately formed a light yellow precipitate. To this was added 12.3 g (0.1 moles) of nicotinic acid in 83.7 g of water and 4.0 g (0.1 moles) of NaOH. As in Example 29 a very light precipitate resulted. This precipitate corresponds to Formula V wherein a is 2, b is 1, M is Mn and R is the residue of the amino acids listed in Table 3 wherein each amino acid is present in its respective mole percent.

The $\pi$-bonded vitamin mineral chelates described herein may be appropriately formulated for administration to warm blooded animals, including humans, in any suitable form. They may be administered orally, by injection or even transdermally. Oral administration is preferable. In many cases, mixing of the chelates in the food, drinking water or other ration form given to the animal may be the preferred method of administration. For example, the chelates may be mixed with salt (sodium chloride) when being administered to certain animal species such as ruminants. In the case of humans, the chelates may be administered in the form of tablets, capsules, powders, syrups, elixirs or any other suitable form. They may be mixed with fillers, excipients, other minerals and/or vitamins and other foodstuffs.

The exact amount of mineral and/or vitamin to be administered, may depend upon the particular need of the animal to which it is administered. It is not feasible to categorically state that "X" mg of trace mineral or vitamin per kg of animal body weight is what is to be administered. For any animal species in which an RDA [recommended dietary allowance], or similar nutritional guideline, has been established for either the mineral or vitamin, that amount may be used as a guideline for determining the "effective" amount to be administered to that species per day. Generally, amounts ranging from about 25 to 500% of the established RDA, or other nutritional guideline, for the mineral being administered may be considered as an "effective amount".

While the above describes the invention in terms of the best mode presently known, the invention is not limited to any specific example or mode demonstrated. The invention is limited only by the following claims and functional equivalents thereof.

I claim:

1. A vitamin mineral chelate having at least one $\pi$-cloud bond formed between the $\pi$ cloud of an aromatic moiety of a water soluble vitamin and the mineral, said chelate having the formula:

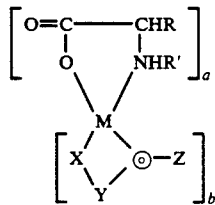

wherein a is an integer of 0, 1 or 2, b is an integer of 1, 2 or 3, with the proviso that the sum of a and b does not exceed 3, the combination of X, Y and ⊙-Z is the residue of said water vitamin wherein X is a member selected from the group consisting of OH, SH and $NH_2$, Y is a member selected from the group consisting of $CH_2$, $CH_2CH_2$, and C(O), ⊙ is the aromatic ring of said water soluble vitamin and Z is the remainder of the residue of said water soluble vitamin not defined by X, Y and ⊙ with the proviso that ⊙, Y and X are configured to form a five or six membered ring structure when bonded to M; R is the residue of any naturally occurring α-amino acid, R' is a member selected from the group consisting of H and $[C(O)CHRNH]_eH$ where e is an integer of 1 or 2, and M is a metal ion selected from the group consisting of Fe, Cu, Mn, Zn, Ca and Mg.

2. A vitamin mineral chelate according to claim 1 wherein Z-⊙, Y and X is the residue of a water soluble vitamin selected from the group consisting of nicotinamide, nicotinic acid, pyridoxine, thiamine, riboflavin and folic acid.

3. A vitamin chelate according to claim 2 wherein M is a metal ion selected from the group consisting of either Cu, Mn and Fe or Zn, Ca and Mg.

4. A vitamin chelate according to claim 3 wherein Z-⊙, Y and X is the residue of nicotinamide with X being $NH_2$, Y being C(O) and ⊙-Z being pyridyl.

5. A vitamin chelate according to claim 4 wherein a is 1, b is 1 and M is a member selected from the group consisting of Zn, Ca and Mg.

6. A vitamin chelate according to claim 4 wherein a is 0, b is 2 and M is a member selected from the group consisting of Zn, Ca and Mg.

7. A vitamin chelate according to claim 4 wherein a is 0, b is 2 and M is a member selected from the group consisting of Cu, Fe and Mn.

8. A vitamin chelate according to claim 4 wherein a is 0, b is 3 and M is a member selected from the group consisting of Cu, Fe and Mn.

9. A vitamin chelate according to claim 3 wherein Z-⊙, Y and X is the residue of nicotinic acid with X being OH, Y being C(O) and ⊙-Z being pyridyl.

10. A vitamin chelate according to claim 9 wherein a is 1, b is 1 and M is a member selected from the group consisting of Zn, Ca and Mg.

11. A vitamin chelate according to claim 9 wherein a is 0, b is 2 and M is a member selected from the group consisting of Zn, Ca and Mg.

12. A vitamin chelate according to claim 9 wherein a is 0, b is 2 and M is a member selected from the group consisting of Cu, Fe and Mn.

13. A vitamin chelate according to claim 9 wherein a is 0, b is 3 and M is a member selected from the group consisting of Cu, Fe and Mn.

14. A vitamin chelate according to claim 3 wherein Z-⊙, Y and X is the residue of pyridoxine with X being OH, Y being $CH_2$, ⊙ is a pyridine ring and Z represents 5-methyl, 4-hydroxy and 3-hydroxymethyl substituents on the pyridine ring.

15. A vitamin chelate according to claim 14 wherein a is 1, b is 1 and M is a member selected from the group consisting of Zn, Ca and Mg.

16. A vitamin chelate according to claim 14 wherein a is 0, b is 2 and M is a member selected from the group consisting of Zn, Ca and Mg.

17. A vitamin chelate according to claim 14 wherein a is 0, b is 2 and M is a member selected from the group consisting of Cu, Fe and Mn.

18. A vitamin chelate according to claim 14 wherein a is 0, b is 3 and M is a member selected from the group consisting of Cu, Fe and Mn.

19. A vitamin chelate according to claim 3 wherein Z-⊙, Y and X is the residue of thiamine with X being OH, Y being $CH_2CH_2$, ⊙ is a thiazole ring and Z represents 3-[(4-amino-2-methyl-5-pyrimidinyl)methyl, and 4-methyl substituents on the thiazole ring.

20. A vitamin chelate according to claim 19 wherein a is 1, b is 1 and M is a member selected from the group consisting of Zn, Ca, and Mg.

21. A vitamin chelate according to claim 19 wherein a is 0, b is 2 and M is a member selected from the group consisting of Zn, Ca and Mg.

22. A vitamin chelate according to claim 19 wherein a is 0, b is 2 and M is a member selected from the group consisting of Cu, Fe and Mn.

23. A vitamin chelate according to claim 19 wherein a is 0, b is 3 and M is a member selected from the group consisting of Cu, Fe and Mn.

24. A vitamin chelate according to claim 3 wherein Z-⊙, Y and X is the residue of riboflavin.

25. A vitamin chelate according to claim 3 wherein Z-⊙, Y and X is the residue of folic acid.

26. A method of concurrently promoting vitamin and mineral uptake in a warm-blooded animal which comprises administering to said warm-blooded animal an effective amount of a vitamin and mineral chelate having at least one $\pi$-cloud bond formed between the π cloud of an aromatic moiety of a water soluble vitamin and the mineral, said chelate having the formula:

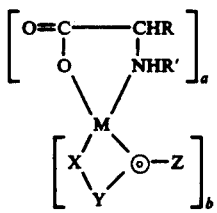

wherein a is an integer of 0, 1 or 2, b is an integer of 1, 2 or 3, with the proviso that the sum of a and b does not exceed 3, the combination of X, Y and ⊙-Z is the residue of said water vitamin wherein X is a member selected from the group consisting of OH, SH and $NH_2$, Y is a member selected from the group consisting of $CH_2$, $CH_2CH_2$, and C(O), ⊙ is the aromatic ring of said water soluble vitamin and Z is the remainder of the residue of said water soluble vitamin not defined by X, Y and ⊙ with the proviso that ⊙, Y and X are configured to form a five or six membered ring structure when bonded to M; R is the residue of any naturally occurring α-amino acid, R' is a member selected from the group consisting of H and $[C(O)CHRNH]_eH$ where e is an integer of 1 or 2, and M is a metal ion selected from the group consisting of Fe, Cu, Mn, Zn, Ca and Mg.

27. A method according to claim 26 wherein, in said chelate, Z-⊙, Y and X is the residue of a water soluble vitamin selected from the group consisting of nicotinamide, nicotinic acid, pyridoxine, thiamine, riboflavin and folic acid.

28. A method according to claim 27 wherein, in said chelate, M is a metal ion selected from the group consisting of either Cu, Mn and Fe or Zn, Ca and Mg.

29. A method according to claim 28 wherein, in said chelate, Z-⊙, Y and X is the residue of nicotinamide with X being $NH_2$, Y being C(O) and ⊙-Z being pyridyl.

30. A method according to claim 29 wherein, in said chelate, a is 1, b is 1 and M is a member selected from the group consisting of Zn, Ca and Mg.

31. A method according to claim 29 wherein, in said chelate, a is 0, b is 2 and M is a member selected from the group consisting of Zn, Ca and Mg.

32. A method according to claim 29 wherein, in said chelate, a is 0, b is 2 and M is a member selected from the group consisting of Cu, Fe and Mn.

33. A method according to claim 29 wherein, in said chelate, a is 0, b is 3 and M is a member selected from the group consisting of Cu, Fe and Mn.

34. A method according to claim 28 wherein, in said chelate, Z-⊙, Y and X is the residue of nicotinic acid with X being OH, Y being C(O) and ⊙-Z being pyridyl.

35. A method according to claim 34 wherein, in said chelate, a is 1, b is 1 and M is a member selected from the group consisting of Zn, Ca and Mg.

36. A method according to claim 34 wherein, in said chelate, a is 0, b is 2 and M is a member selected from the group consisting of Zn, Ca and Mg.

37. A method according to claim 34 wherein, in said chelate, a is 0, b is 2 and M is a member selected from the group consisting of Cu, Fe and Mn.

38. A method according to claim 34 wherein, in said chelate, a is 0, b is 3 and M is a member selected from the group consisting of Cu, Fe and Mn.

39. A method according to claim 28 wherein, in said chelate, Z-⊙, Y and X is the residue of pyridoxine with X being OH, Y being $CH_2$, ⊙ is a pyridine ring and Z represents 5-methyl, 4-hydroxy and 3-hydroxymethyl substituents on the pyridine ring.

40. A method according to claim 39 wherein, in said chelate, a is 1, b is 1 and M is a member selected from the group consisting of Zn, Ca and Mg.

41. A method according to claim 39 wherein, in said chelate, a is 0, b is 2 and M is a member selected from the group consisting of Zn, Ca and Mg.

42. A method according to claim 39 wherein, in said chelate, a is 0, b is 2 and M is a member selected from the group consisting of Cu, Fe and Mn.

43. A method according to claim 39 wherein, in said chelate, a is 0, b is 3 and M is a member selected from the group consisting of Cu, Fe and Mn.

44. A method according to claim 28 wherein, in said chelate, Z-⊙, Y and X is the residue of thiamine with X being OH, Y being $CH_2CH_2$, ⊙ is a thiazole ring and Z represents 3-[(4-amino-2-methyl-5-pyrimidinyl)-methyl, and 4-methyl substituents on the thiazole ring.

45. A method according to claim 44 wherein, in said chelate, a is 1, b is 1 and M is a member selected from the group consisting of Zn, Ca, and Mg.

46. A method according to claim 44 wherein, in said chelate, a is 0, b is 2 and M is a member selected from the group consisting of Zn, Ca and Mg.

47. A method according to claim 44 wherein, in said chelate, a is 0, b is 2 and M is a member selected from the group consisting of Cu, Fe and Mn.

48. A method according to claim 44 wherein, in said chelate, a is 0, b is 3 and M is a member selected from the group consisting of Cu, Fe and Mn.

49. A method according to claim 28 wherein, in said chelate, Z-⊙, Y and X is the residue of riboflavin.

50. A method according to claim 28 wherein, in said chelate, Z-⊙, Y and X is the residue of folic acid.

* * * * *